US 6,504,288 B2

United States Patent
Lewis

(10) Patent No.: US 6,504,288 B2
(45) Date of Patent: Jan. 7, 2003

(54) COMPENSATED INDIVIDUALLY ADDRESSABLE ARRAY TECHNOLOGY FOR HUMAN BREAST IMAGING

(75) Inventor: D. Kent Lewis, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/730,640

(22) Filed: Dec. 5, 2000

(65) Prior Publication Data
US 2002/0067107 A1 Jun. 6, 2002

(51) Int. Cl.[7] .............................................. H01L 41/107
(52) U.S. Cl. ...................................... 310/334; 310/318
(58) Field of Search ................................. 310/322, 334, 310/318

(56) References Cited

U.S. PATENT DOCUMENTS

| | | | | | |
|---|---|---|---|---|---|
| 4,155,259 A | * | 5/1979 | Engeler | ....................... | 73/626 |
| 4,281,550 A | * | 8/1981 | Erikson | ....................... | 73/626 |
| 4,452,084 A | * | 6/1984 | Taenzer | ....................... | 73/609 |
| 4,511,998 A | * | 4/1985 | Kanda et al. | ............... | 310/334 |
| 4,961,176 A | * | 10/1990 | Tanaka et al. | ............... | 367/155 |
| 5,316,000 A | * | 5/1994 | Chapelon et al. | ........... | 310/334 |
| 5,738,635 A | * | 4/1998 | Chapelon et al. | ............... | 601/2 |
| 5,744,898 A | * | 4/1998 | Smith et al. | ................. | 310/334 |
| 5,793,701 A | * | 8/1998 | Wright et al. | ................... | 367/7 |
| 5,856,955 A | * | 1/1999 | Cole et al. | .................... | 367/138 |
| 5,873,845 A | * | 2/1999 | Cline et al. | ..................... | 601/2 |
| 5,945,770 A | * | 8/1999 | Hanafy | ....................... | 310/334 |
| 6,029,116 A | * | 2/2000 | Wright et al. | ................. | 702/32 |
| 6,043,590 A | * | 3/2000 | Gilmore | ..................... | 310/367 |
| 6,110,116 A | * | 8/2000 | Wrigth et al. | ............... | 600/447 |
| 6,168,565 B1 | * | 1/2001 | Napolitano | ................. | 600/447 |
| 6,172,939 B1 | * | 1/2001 | Cole et al. | ................... | 367/138 |

FOREIGN PATENT DOCUMENTS

WO PCT/AU82/00187 * 6/1983 ........... A61B/10/00

* cited by examiner

Primary Examiner—Thomas M. Dougherty
(74) Attorney, Agent, or Firm—L. E. Carnahan; Alan H. Thompson

(57) ABSTRACT

A method of forming broad bandwidth acoustic or microwave beams which encompass array design, array excitation, source signal preprocessing, and received signal postprocessing. This technique uses several different methods to achieve improvement over conventional array systems. These methods are: 1) individually addressable array elements; 2) digital-to-analog converters for the source signals; 3) inverse filtering from source precompensation; and 4) spectral extrapolation to expand the bandwidth of the received signals.

The components of the system will be used as follows:

1) The individually addressable array allows scanning around and over an object, such as a human breast, without any moving parts. The elements of the array are broad bandwidth elements and efficient radiators, as well as detectors.

2) Digital-to-analog converters as the source signal generators allow virtually any radiated field to be created in the half-space in front of the array.

3) Preprocessing allows for corrections in the system, most notably in the response of the individual elements and in the ability to increase contrast and resolution of signal propagating through the medium under investigation.

4) Postprocessing allows the received broad bandwidth signals to be expanded in a process similar to analytic continuation.

Used together, the system allows for compensation to create beams of any desired shape, control the wave fields generated to correct for medium differences, and improve contract and resolution in and through the medium.

11 Claims, 3 Drawing Sheets

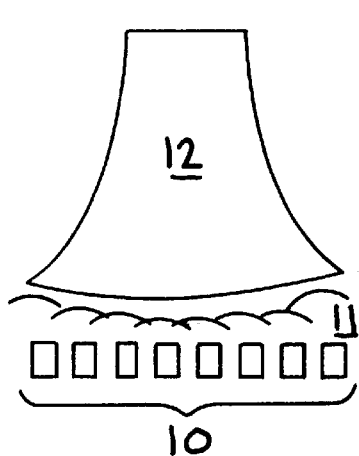
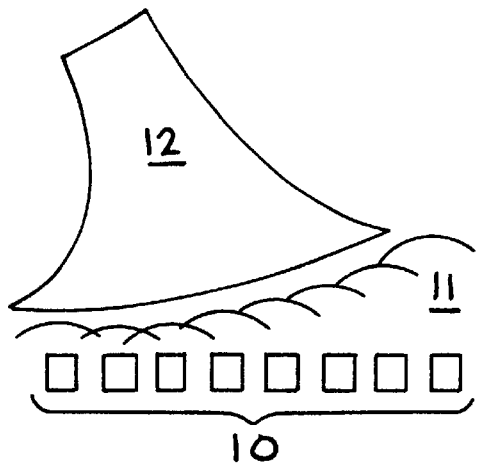
FIG. 1A  FIG. 1B
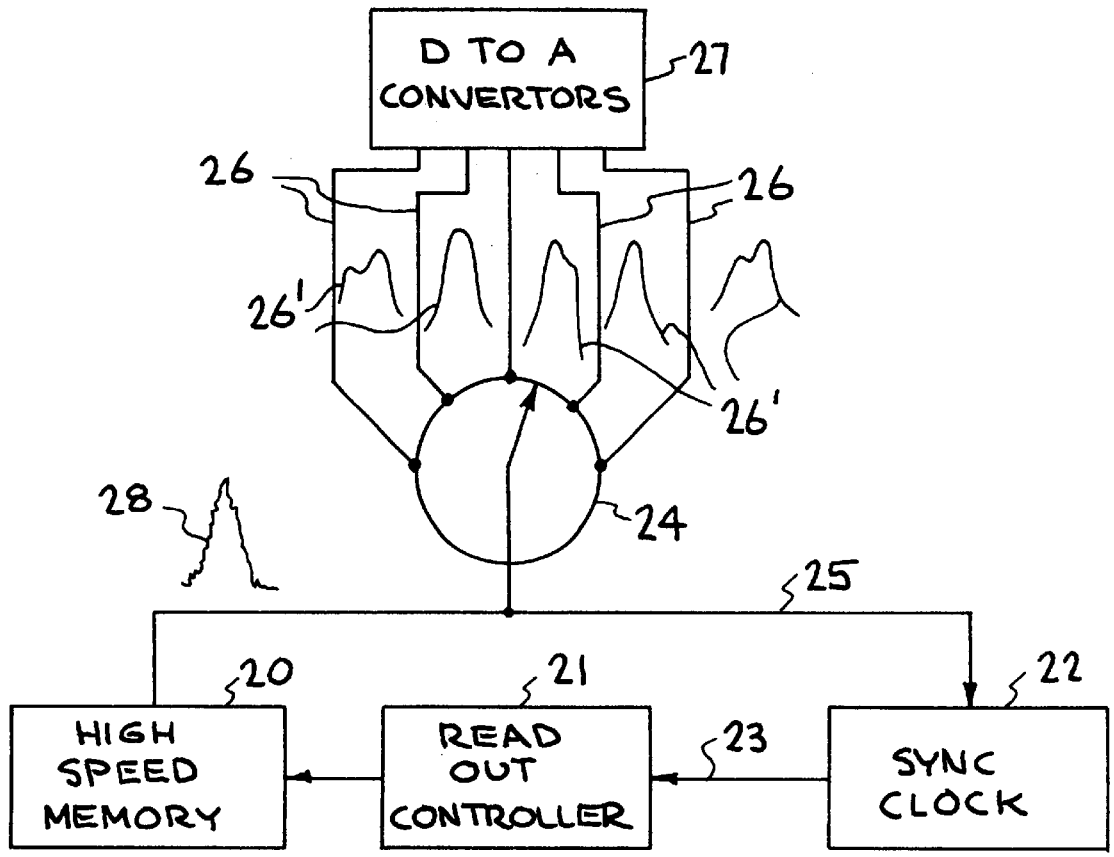
FIG. 2

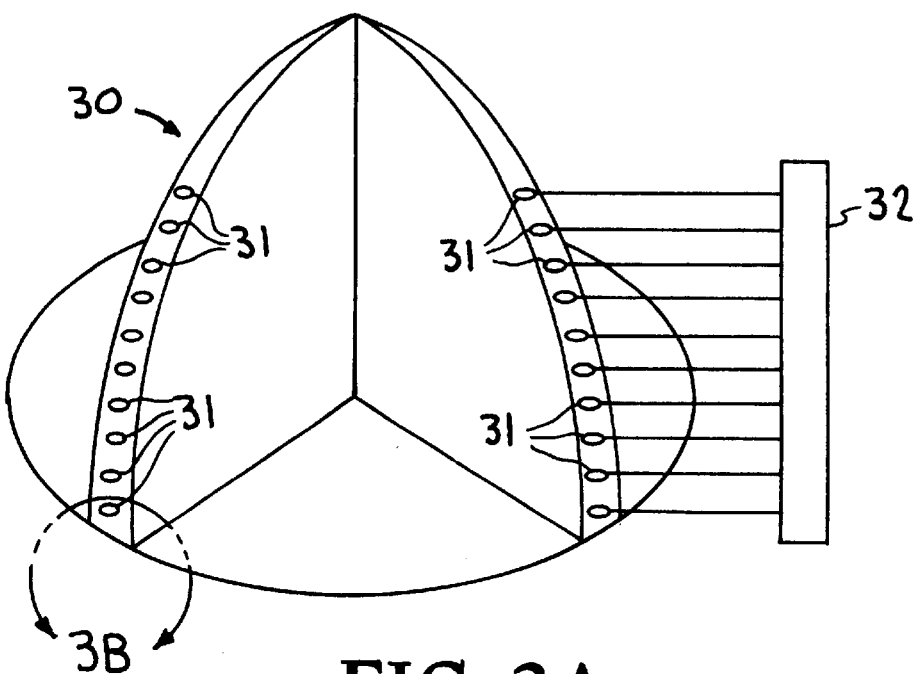
FIG. 3A
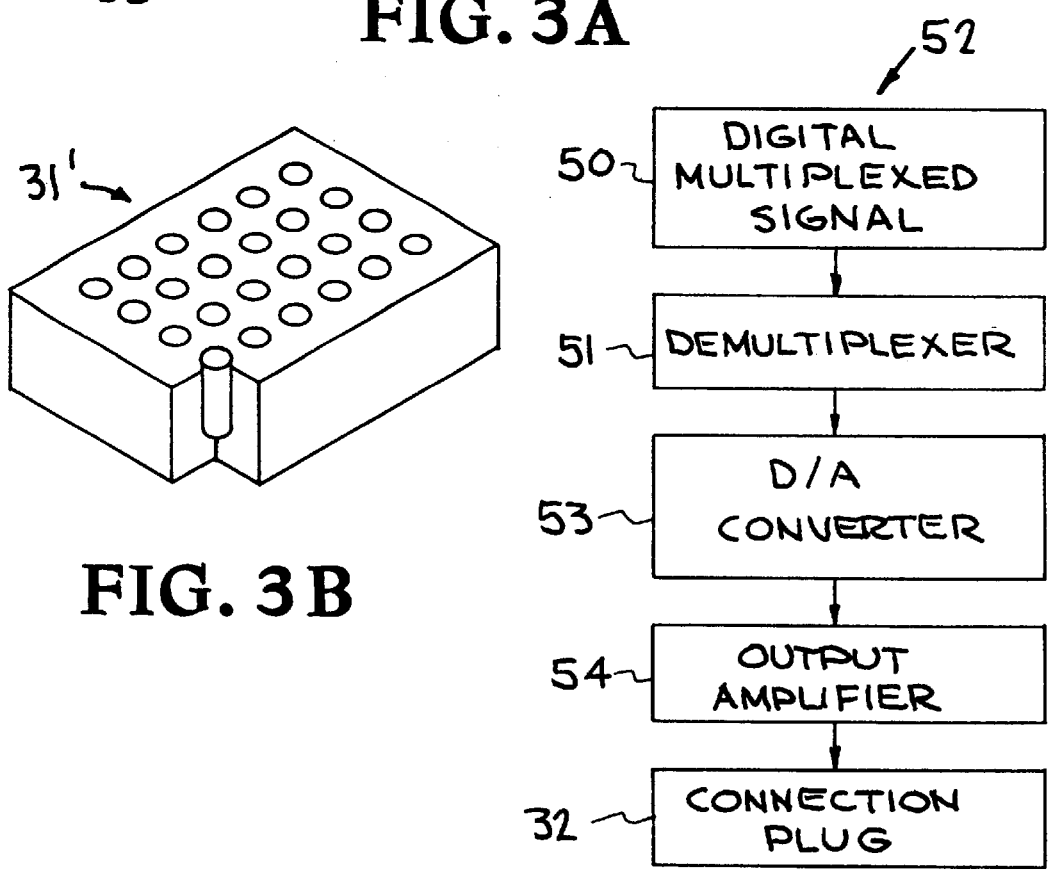
FIG. 3B
FIG. 5

COMPENSATED INDIVIDUALLY ADDRESSABLE ARRAY TECHNOLOGY FOR HUMAN BREAST IMAGING

COMPENSATED INDIVIDUALLY ADDRESSABLE ARRAY TECHNOLOGY

The United States Government has rights in this invention pursuant to Contract No. W-7405-ENG-48 between the United States Department of Energy and the University of California for the operation of Lawrence Livermore National Laboratory.

BACKGROUND OF THE INVENTION

In recent years, a technology has been developed which involves individually addressable array elements, digital to analog converters for the source signals, inverse filtering for source precompensation, and spectral extrapolation to expand the bandwidth of the received signals. This technology provides significant improvement over conventional array systems. This technology has been utilized experimentally in acoustic and microwave projects as a way of forming a precompensated beam and detecting signals with higher than expected resolution.

The present invention involves modifications of this recently developed technology to enable its use, for example, in bio-med scanning and nondestructive evaluation for research and industry; and, more particularly, to scanning and imaging of the human breast.

There are three (3) major pieces or sections to this technique: 1) design of multi-channel, individually-addressable array elements, and associated drive electronics for creating and detecting acoustic and microwave fields; 2) inverse filtering to precompensate the output signals, to correct for flaws in the construction of the array, changing conditions in the propagation media, and so on; and 3) postprocessing, including spectral extrapolation and de-convolution to increase resolution of the system. More specifically, the present invention involves a method of forming acoustic beams encompassing array design, array excitation, and source signal preprocessing. The system of the present invention consists of a shaped array to conform to the breast, drive and detection electronics, and pulse conditioning software to optimize contrast and resolution in a given medium real time.

SUMMARY OF THE INVENTION

It is an object of the present invention to provide a method of forming broad bandwidth acoustic or microwave beams.

A further object of the invention is to provide a method of forming broad bandwidth beams which encompass array design, array excitation, source signal preprocessing, and received signal postprocessing.

Another object of the invention is to provide a technique for imaging human breasts, for example, which involves individually addressable array elements, digital-to-analog converters for the source signals, inverse filtering for source precompensation, and spectral extrapolation to expand the bandwidth of the received signals.

Other objects and advantages of the present invention will become apparent from the following description and accompanying drawings. Basically, the present invention involves compensated, individually addressable array technology. More specifically, this invention involves a method of forming acoustic beams encompassing array design, array excitation, and signal preprocessing, and is particularly applicable for bio-med scanning technologies, such as imaging the human breast.

There are three (3) major pieces to this technique:
1) Design of multi-channel, individually addressable array elements and associated drive electronics for creating and detecting acoustic and microwave fields;
2) Inverse filtering to precompensate the output signals, to correct for flaws in the construction of the array, changing conditions in the propagation media; and
3) Postprocessing, including spectral extrapolation and de-convolution into increase resolution of the system.

BRIEF DESCRIPTION OF THE DRAWINGS

The accompanying drawings, which are incorporated into and form a part of the disclosure, illustrate embodiments of the invention and, together with the description, serve to explain the principles of the invention.

FIGS. 1A and 1B illustrate different beam configurations created by the individually controlled array elements.

FIG. 2 schematically illustrates a data system which includes a high-speed memory and ring distributor, and the data can be released by a byte at a time by a read-out controller synchronized by a clock.

FIGS. 3A and 3B schematically illustrate a micropiezo-electric arch array arrangement made in accordance with the present invention.

FIG. 5 illustrates an embodiment of a multiplexing and A/D conversion assembly made in accordance with the present invention.

DETAILED DESCRIPTION OF THE INVENTION

Figure 4:
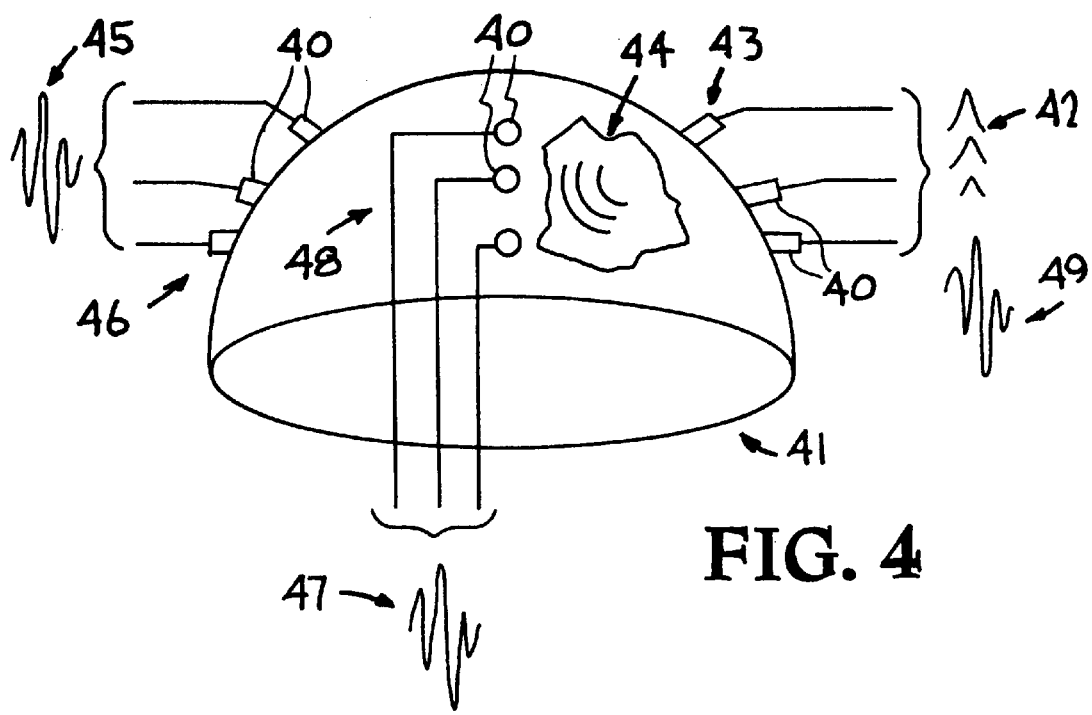
FIG. 4 schematically illustrates an array cap with elements embedded in a matrix that conforms to a desired shape.

The present invention involves compensated, individually addressable array technology. More specifically, the invention involves a method of forming acoustic or microwave beams encompassing array design, array excitation, and source signal preprocessing. This method has applicability to bio-med scanning technologies, for example, and particularly for imaging of the human breast. The system for carrying out the breast imaging application consists of a shaped array to conform to the breast, drive and detection electronics, and pulse conditioning software to optimize contrast and resolution in a given medium real time.

The technique of the present invention uses several different methods to achieve improvement over conventional array systems. These methods include: 1) individually addressable array elements; 2) digital to analog converters for the source signals; and 3) inverse filtering for source precompensation. In addition, spectral extrapolation to expand the bandwidth of the received signals may be used.

The components of the system are used as follows:
1) The individually addressable array allows scanning around and over an object (in this case the human breast) without any moving parts. The elements of the array are broad bandwidth elements and efficient radiators, as well as detectors. Array materials include PVDF piezoelectric plastics, prestressed ceramic tonplitz elements, and 1–3 composite arrays in a shaped matrix board, these materials being known in the art.

2) Digital-to-analog converters as the source signal generator allow virtually any radial field to be created in the half-space in front of the array. The array becomes a virtual part of the computer system.
3) Preprocessing allows for corrections in the system, most notably in the response of the individual elements and in the ability to increase contrast and resolution of signals propagating through the medium under investigation.
4) Postprocessing allows the received broad bandwidth signals to be expanded in a process similar to analytic continuation. A region of high signal to noise is used to create a complex spectrum that is then extended into both higher and lower ranges of frequency space. This spectrum is then inverted and the new signal is measurably sharper than the original.

Used together, the system allows for compensation to create beams of any desired shape, control the wave fields generated to correct for medium differences, and improve contrast and resolution in and through the medium.

The invention is broadly illustrated in FIGS. 1A and 1B, wherein different beams of desired shape are created by different array elements, generally indicated at 10 produce wave fronts, generally indicated at 11 which produce the formed beam intensity, generally indicated at 12. FIGS. 1A and 1B illustrate the ability to address the individual elements with phased (differently delayed) signals that allow the formation of beams and the steering of these beams. The ability to control the frequency-based width and frequency spectral shape of the signals allows for different beam characteristics. The ability to send entirely different signals to each of the array elements allows one to create any desired wave field in the medium to enhance the resolution and contrast at any given location.

There are three (3) major pieces to this technique: 1) design of multi-channel individually addressable array elements and associated drive electronics for creating and detecting acoustic and microwave fields; 2) inverse filtering to precompensate the output signals to correct for flaws in the construction of the array, changing conditions in the propagation media, and so on; and 3) postprocessing, including spectral extrapolation and deconvolution to increase resolution of the system.

The hardware systems for carrying out this method of the present invention are those parts of the device which physically interact with the tissue under investigation. They must create specified initial wave fields, detect the results of those fields traveling through the tissue, and get the relevant data back to the data acquisition computer in a timely manner. The acoustic sound pressure levels must be safe for the tissue, of appropriate frequency range for any given measurement, and detectable. The hardware systems are broken out into three (3) basic functions: 1) signal source system (source generation); 2) transduction system (transduction); and 3) input system (signal input). Source generation involves creating and delivering individually tailored source signals of sufficient electrical power to the transducers. Transduction involves converting these signals into mechanical energy (sound) and launching that energy into the tissue, as well as converting the energy from the tissue arriving at the array into electrical signals. Signal input involves getting all of these signals back into the data acquisition computer in a usable form.

Source Generation:

The source generation or signal source system can be composed of four (4) sequential sections to create acoustic wave fields that will travel through the tissue. The fields are adaptive so that the shape and bandwidth of each pulse can be tailored for maximum contrast and resolution of individual scattering objects. Additionally, the measurements of frequency-dependent attenuation can be made more precise.

The first section is the signal source, which is a fast addressable memory. This gives the ability to generate single frequency tone bursts, square edge pulses, or arbitrary waveforms. Such memory is readily available and will work at speeds of hundreds of millions, to billions, of samples per second. This will provide signals with bandwidths 100's of megahertz, allowing one to multiplex the signals that will actually be used. The system will have sufficient memory to make corrections to the sources signals to correct for mismatch between source transducer and media, and some anticipated signal line reflections. This is a linear system, so precorrections will account for all the anticipated problems.

The second section is a demultiplexing system that will create many different signals out of a single memory entry. These work on the principle of a rotating gate switch, allowing the interleaved memory record to be sent to different output lines. These circuits are essentially computer busses, and run at 10's to 100's of megahertz, again allowing the necessary bandwidth in the demultiplexed signals.

The third section is a fast digital-to-analog (D/A) converter. Similar to those used in consumer compact disk players, these high-speed digital-to-analog converters are fast, reliable, and relatively inexpensive. They will need to work only at the highest necessary frequency, 10 megahertz. The digital-to-analog converters have sufficient speed to generate multiple desired signals without distortion.

The fourth section is the output power amplifier array, ideally one for each array element. The needs here are wide bandwidth, low power, low noise, small size, and low cost. The power amplifiers are high efficiency, low output power, with a frequency bandwidth matching the digital-to-analog converter capability. Their output levels are controlled by a feedback loop from the receive system.

As seen in FIG. 2, the data to be outputted is stored in a fast, high speed memory 20 and released a byte at a time by a read out controller 21. The controller 21 is synchronized by a sync clock 22, as indicated by arrow 23. The clock 22 controls a byte ring distributor 24, as indicated by arrow 25, which is a high speed switch system that loads each byte into separate channels indicated at 26, each with a different signal as indicated at 26. The demultiplexed data streams or channels 26 (five shown) are then fed to relatively low speed digital-to-analog converters 27 (five shown), filtered, and outputted as separate analog voltages. The composite signal 28 is a composite of the separated smooth output signals. The cost savings are in the use of the relatively low-speed digital-to-analog converters 27.

Transduction:

The transduction system must be both efficient in creating acoustic energy and sensitive enough to detect low levels of scattered energy and higher levels of transmitted and reflected energy. Thus, the array head is composed of high efficiency elements able to radiate and detect over a broad frequency bandwidth. Further, the elements must be distributed densely enough to introduce the energy necessary for field creation and to detect the scattered fields finely enough for the imaging algorithms to unfold the volumetric picture in sufficient detail for analysis. Thus, the output power is kept low to avoid causing any tissue damage in the scan mode, and sparse enough to avoid any element-to-element cross talk. Finally, the elements must be in the right place for almost any measurement to be made.

These requirements led to a hemispherical cap or head design which allows almost total coverage of breast tissue.

The head will be composed of a rigid hemisphere which couples to the breast through a water bath, or comprises a pliable cup which can conform to the breast shape and couples directly into the tissue. Also, pliable concentric rings or an adjustable tree structure may be utilized. The materials composing the array elements may be either a PZT embedded in a matrix, a PVDF copolymer, PVDF piezoelectric plastics, prestressed ceramic tonplitz elements, and 1–3 composite arrays.

FIGS. 3A and 3B illustrate a micropiezoelectric "arch" array coupled to a connecting plug. Coupling the source and detector circuitry to the array elements is possible in many different ways. The limit of one's ability to connect the array to the device is currently a center-to-center separation between elements of 25 microns or $\frac{1}{1000}$ inch, far more than needed. As shown in FIGS. 3A and 3B, the arch or cup 30 includes numerous array elements 31 connected to a connecting plug 32. The array elements 31 are shown slightly enlarged at 31', and greatly enlarged in FIG. 3B. As shown in FIG. 3B, the elements 31 comprise PZT rods in polymer 2 mm thick for 1 megahertz, and 0.2 mm for 10 megahertz. The connection to the connecting plug 32 will be described hereinafter with respect to FIG. 5, showing the "input section."

FIG. 4 illustrates a preferred embodiment of a cup or head incorporating an acoustic element array. The elements 40 are embedded in a matrix or cup 41 that conforms to the desired shape (a human breast). The elements 40 fill the entire array cup 41, only a few elements being shown. The input signals 42, generated by the digital-to-analog converters (see FIG. 2) are sent to a set of elements indicated at 43, and an acoustic wave field 44 is generated in the tissue located beneath the cup 41. The transmitted signal indicated at 45 is detected by some of the receiving elements indicated at 46. The scattered signals indicated at 47 are detected by other receiving elements indicated at 48, and the reflected signals indicated at 49 are detected by the original elements indicated at 43.

The received and transmitted signals 45 are then digitized and multiplexed before being fed to the control computer. Those signals can be taken sequentially around the array cup 41 as the transmitter continues to send a short pulse relative to the repetition rate. The control computer separates the different signals and presents them for further analysis.

Signal Input:

The input system is computer controllable and able to transfer vast amounts of time signals to the algorithms for analysis. It, too, is a multiplexed system (see FIG. 5), with the analog signals of each individual array element sampled at a sufficiently high rate to match the required frequency bandwidth. A fast switching network and fast analog-to-digital converters are used to make the data digital. The input system delivers the detected and postprocessed signals to the reconstruction algorithms. It consists of multiple preamplifiers and a multiplexer system to speed and simplify the data transfer. The input multiplexers will be synced to the clock speeds of the digital-to-analog converters for simplicity.

Referring now to FIG. 5, a digital multiplexed signal 50 passes through a demultiplexer 51 via a controller 52 to a digital-to-analog converter 53, and the output from converter 53 passes through an output amplifier 54 to a connection plug 32 (as seen in FIG. 3A) for connection to an array element.

Figure 6:
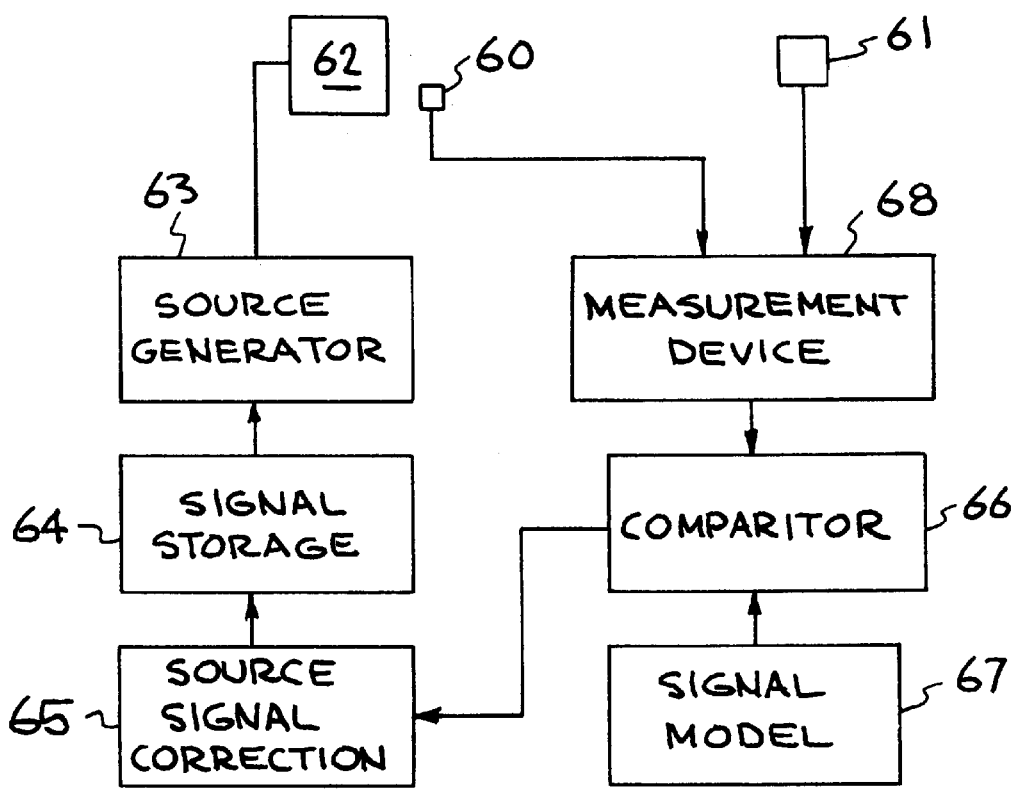
FIG. 6 illustrates in diagram form the signal processing in accordance with the invention.

FIG. 6 diagrammatically illustrates the signal sequence of the apparatus of FIGS. 2–5. What is being illustrated in FIG. 6 is, that for any element or group of elements, including the entire set of elements, the near field sensor 60, or the far field sensor 61 response of the medium to an array (or multi-element array) 62 or the element itself can be measured and compared to what is expected. While a model of the system is implied in FIG. 6 for each system, the model is different. Once the response is measured, wherever and however, a correction to the source signal can be made and a closer approximation to the desired response achieved. The system as shown in FIG. 6 additionally includes a source generator 63 for directing a signal to array element 62, signal storage 64, source signal correction 65, comparitor (comparison to expected signal) 66, signal model (expected responses) 67, and a measurement device (transient digitizer) 68 for receiving signals from the near field sensor 60 and the far field sensor 61. The near field sensor 60 may be a contact or proximity detector or interferometer which detects pressure, displacement, velocity or acceleration. The far field sensor may be an interferometer that detects pressure, displacement, velocity, or acceleration. The source generator 63 may be a digital-to-analog converter or tuned transmission line. The signal storage 64 may be digital or tuning (mechanical).

It has thus been shown that the present invention provides an apparatus and method of forming broad bandwidth acoustic beams encompassing array design, array excitation, and source signal preprocessing. The system consists of a shaped array to conform to the human breast, for example, with drive and detection electronics, plus pulse conditioning software, to optimize contrast and resolution in a given medium real time.

While particular embodiments and components, etc., have been described and/or illustrated to exemplify and teach the principles of the present invention, such are not intended to be limiting. Modifications and changes may become apparent to those skilled in the art, and it is intended that the invention be limited only by the scope of the appended claims.

What is claimed is:

1. A method of imaging human breasts including forming broad band acoustic or microwave beams which encompasses:

providing a breast conforming array head:

said breast conforming array head having a configuration selected from the group consisting of a hemispherical cup, a shape-conforming cup, and concentric rings of different size;

providing a multi-channel individually addressable array of elements on the array head to form arbitrary voltage signals as a function of time;

providing array excitation by operatively connecting drive electronics to the array of elements for creating and detecting acoustic and microwave fields, the operatively connecting of the drive electronics being carried out by providing source signal generators connected to each of the elements of the array, the providing of the source signal generators being carried out using a high-speed memory operatively connected to a read-out controller to release a byte at a time to a byte distributor operatively connected to digital-to-analog converters, and controlling the read-out controller and the byte distributor by a synchronized clock, providing source signal processing; and providing received signal postprocessing.

2. The method of claim 1, wherein providing the array of elements is carried out by providing an array of piezoelectric material arranged in an array configuration and mounted in a supporting matrix.

3. The method of claim 2, wherein providing an array of piezoelectric material is carried out using a material selected from the group consisting of a PZT embedded in a matrix, PVDF and associated copolymers with conductive coatings painted or sputtered on a matrix arrangement, PVDF piezoelectric plastics, a PZT embedded in a cloth-like matrix, and prestressed ceramic tonplitz elements.

4. The method of claim 2, wherein the array configuration is mounted in a supporting matrix of said breast conforming array head.

5. The method of claim 1, wherein the source signal generators comprise digital-to-analog converters.

6. An apparatus for imaging human breasts by forming broad bandwidth acoustic beams, including:

a breast conforming array head;

said breast conforming array head being selected from the group consisting of a hemispherical cup, a shape-conforming cup, and concentric rings of different sizes;

individually addressable array elements mounted to said array head for forming arbitrary voltage signals as a function of time;

means for providing excitation of the array ahead;

said means including source signal generators connected to each of the elements of the array, said source signal generators including a high-speed memory operatively connected to a read-out controller to release a byte at a time to a byte distributor operatively connected to digital-to-analog converters, and a synchronized clock for controlling the read-out controller and the byte distributor;

means for supplying source signals to each of the array elements;

means for inverse filtering for source precompensation; and means for providing spectral extrapolation to expand the bandwidth of received signals.

7. The apparatus of claim 6, wherein said array elements are selected from the group consisting of a PZT embedded in a matrix, PVDF and associated copolymers with conductive coatings painted or sputtered on a matrix arrangement, a PZT embedded in a cloth-like matrix, and prestressed ceramic tonplitz elements.

8. The apparatus of claim 6, wherein said means for supplying source signals to each of the array elements includes digital-to-analog converters operatively connected to said array elements.

9. The apparatus of claim 8, wherein said means for supplying source signals to each of the array elements additionally includes a byte distributor operatively connected to said digital-to-analog converters, a high-speed memory operatively connected to said byte distributor, a read out controller operatively connected to said high-speed memory, and a sync clock operatively connected to each of said byte distributor and said read-out controller.

10. The apparatus of claim 9, wherein said digital-to-analog converters are connected to said array elements via a connector plug.

11. The apparatus of claim 6, wherein said means for at least inverse filtering for source precompensation includes means for providing a digital multiplexed signal, a demultiplexer, a digital-to-analog converter, and an output amplifier operatively connected to said array elements via a connector plug.

* * * * *